(12) United States Patent
Kuimelis et al.

(10) Patent No.: US 6,537,749 B2
(45) Date of Patent: *Mar. 25, 2003

(54) ADDRESSABLE PROTEIN ARRAYS

(75) Inventors: Robert G. Kuimelis, Brighton, MA (US); Richard Wagner, Concord, MA (US)

(73) Assignee: Phylos, Inc., Lexington, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/282,734

(22) Filed: Mar. 31, 1999

(65) Prior Publication Data

US 2002/0182597 A1 Dec. 5, 2002

Related U.S. Application Data

(60) Provisional application No. 60/080,686, filed on Apr. 3, 1998.

(51) Int. Cl.[7] .......................... C12Q 1/68; C12P 21/06; G01N 33/534; C07H 21/02
(52) U.S. Cl. .......................... 435/6; 435/68.1; 436/518; 536/23.1
(58) Field of Search ................ 435/6, 68.1; 436/518; 536/23.1

(56) References Cited

U.S. PATENT DOCUMENTS

| | | | |
|---|---|---|---|
| 5,143,854 A | | 9/1992 | Pirrung et al. ............... 436/518 |
| 5,514,543 A | * | 5/1996 | Grossman et al. ............. 435/6 |
| 5,545,531 A | | 8/1996 | Rava et al. ..................... 435/6 |
| 5,545,698 A | * | 8/1996 | Barany et al. ............... 525/420 |
| 5,547,835 A | * | 8/1996 | Koster ............................ 435/6 |
| 5,556,752 A | | 9/1996 | Lockhart et al. ............... 435/6 |
| 5,623,065 A | * | 4/1997 | Cook et al. ................. 536/23.1 |
| 5,627,024 A | | 5/1997 | Maruyama et al. |
| 5,643,768 A | | 7/1997 | Kawasaki |
| 5,677,196 A | * | 10/1997 | Herron et al. ............... 436/518 |
| 5,789,208 A | | 8/1998 | Sharon |
| 5,843,701 A | * | 12/1998 | Gold et al. ................. 435/68.1 |
| 5,849,878 A | | 12/1998 | Cantor et al. |
| 5,935,793 A | * | 8/1999 | Wong et al. ..................... 435/6 |
| 5,965,133 A | | 10/1999 | Cantor et al. |
| 5,972,615 A | * | 10/1999 | An et al. ......................... 435/6 |
| 5,985,575 A | | 11/1999 | Wickens et al. |
| 6,207,446 B1 | | 3/2001 | Szostak et al. |
| 6,214,553 B1 | * | 4/2001 | Szostak et al. |
| 6,258,558 B1 | | 7/2001 | Szostak et al. |
| 6,261,804 B1 | | 7/2001 | Szostak et al. |
| 6,281,344 B1 | | 8/2001 | Szostak et al. |

FOREIGN PATENT DOCUMENTS

| | | | |
|---|---|---|---|
| EP | 0742287 | * | 9/1996 |
| WO | WO 92/10092 | | 6/1992 |
| WO | WO 92/10588 | | 6/1992 |
| WO | WO 93/03172 | | 2/1993 |
| WO | WO 95/11922 | | 5/1995 |
| WO | WO 96/22391 | | 7/1996 |
| WO | WO 97/27317 | * | 7/1997 |
| WO | WO 98/31700 | | 7/1998 |

OTHER PUBLICATIONS

Pieles et al., "Preparation of a novel psoralen containing deoxyadenosine building block for the facile solid phase synthesis of psoralen–modified oligonucleotides for a sequence specific cross–link . . . " Nucleic Acids Research vol. 17, pp. 8967–8978, 1989.*

Guo et al. "Direct fluorescence analysis of genetic polymorphisms by hybridization with oligonucleotide arrays on glass supports" Nucleic Acids Research, vol. 22, pp. 5456–5465, 1994.*

Husimi et al., "Role of the Virus–Type Strategy in Encoded Molecular Evolution," Progress in Biophysics and Molecular Biology, vol. 65 (Suppl. 1), Abstract P–A5–04 (1996).

Pease et al., "Light–Generated Oligonucleotide Arrays for Rapid DNA Sequence Analysis," *Proc. Natl. Acad. Sci. USA* 91:5022–5026 (1994).

Lipshutz et al., "Using Oligonucleotide Probe Arrays to Access Genetic Diversity," *BioTechniques* 19:442–447 (1995).

Raynaud et al., "Synthesis and Characterization of $O^6$—Modified Deoxyguanosine–Containing Oligodeoxyribonucleotides for Triple–Helix Formation," *Tetrahedron* 52:2047–2064 (1996).

Guo et al., "Direct Fluorescence Analysis of Genetic Polymorphisms by Hybridization with Oligonucleotide Arrays on Glass Supports," Nucleic Acids Research 22:5456–5465 (1994).

Maskos et al., "Parallel Analysis of Oligodeoxyribonucleotide (Oligonucleotide) Interactions. I. Analysis of Factors Influencing Oligonucleotide Duplex Formation," Nucleic Acids Research 20:1675–1678 (1992).

Niemeyer et al., "Oligonucleotide–Directed Self–Assembly of Proteins: Semisynthetic DNA–Streptavidin Hybrid Molecules as Connectors For the Generation of Macroscopic Arrays and the Construction of Supramolecular Bioconjugates," Nucleic Acids Research 22:5530–5539 (1994).

Roberts et al., "RNA–Peptide Fusions for the In Vitro Selection of Peptides and Proteins," Proc. Natl. Acad. Sci. USA 94:12297–12302 (1997).

Schena et al., "Quantitative Monitoring of Gene Expression Patterns with a Complementary DNA Microarray," Science 270:467–470 (1995).

* cited by examiner

*Primary Examiner*—Kenneth R. Horlick
*Assistant Examiner*—Young Kim
(74) *Attorney, Agent, or Firm*—Clark & Elbing

(57) ABSTRACT

Disclosed herein are arrays of nucleic acid-protein fusions which are immobilized to a solid surface through capture probes which include a non-nucleosidic spacer group and an oligonucleotide sequence to which the fusion (such as an RNA-protein fusion) is bound. Also disclosed herein are solid supports on which these arrays are immobilized as well as methods for their preparation and use (for example, for screening for protein-compound interactions such as protein-therapeutic compound interactions).

29 Claims, 6 Drawing Sheets

Fig. 6

SEQUENCE LISTING

<160> NUMBER OF SEQ ID NOS: 29

<210> SEQ ID NO 1
<211> LENGTH: 99
<212> TYPE: RNA
<213> ORGANISM: Artificial Sequence
<220> FEATURE:
<223> OTHER INFORMATION: Oligonucleotide employed to construct FLAG
      epitope fusion

<400> SEQUENCE: 1
uaauacgacu cacuauaggg acaauuacua uuuacaauua caauggacua caaggacgau    60
gacgauaagg gcggcugguc ccaccccag uucgagaag                            99

<210> SEQ ID NO 2
<211> LENGTH: 102
<212> TYPE: RNA
<213> ORGANISM: Artificial Sequence
<220> FEATURE:
<223> OTHER INFORMATION: Oligonucleotide employed to construct HA11
      epitope fusion

<400> SEQUENCE: 2
uaauacgacu cacuauaggg acaauuacua uuuacaauua caauguaccc cuacgacgug    60
cccgacuacg ccggcggcug gucccacccc caguucgaga ag                      102

<210> SEQ ID NO 3
<211> LENGTH: 29
<212> TYPE: DNA
<213> ORGANISM: Artificial Sequence
<220> FEATURE:

```
<223> OTHER INFORMATION: Oligonucleotide used for attaching puromycin

<400> SEQUENCE: 3
aaaaaaaaaa aaaaaaaaaa aaaaaaacc                                29

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide used for chip attachment

<400> SEQUENCE: 4
tgtaaatagt aattgtccc                                           19

<210> SEQ ID NO 5
<211> LENGTH: 14
<212> TYPE: DNA
<213> ORGANISM: Artificial Sequence
<220> FEATURE:
<223> OTHER INFORMATION: Oligonucleotide used for chip attachment

<400> SEQUENCE: 5
cttctcgaac tggg                                                14

<210> SEQ ID NO 6
<211> LENGTH: 15
<212> TYPE: DNA
<213> ORGANISM: Artificial Sequence
<220> FEATURE:
<223> OTHER INFORMATION: Oligonucleotide used for chip attachment

<400> SEQUENCE: 6
cctgtaggtg tccat                                               15

<210> SEQ ID NO 7
<211> LENGTH: 15
<212> TYPE: DNA
<213> ORGANISM: Artificial Sequence
<220> FEATURE:
<223> OTHER INFORMATION: Oligonucleotide used for chip attachment

<400> SEQUENCE: 7
caggtagaag tcggt                                               15

<210> SEQ ID NO 8
<211> LENGTH: 16
<212> TYPE: DNA
<213> ORGANISM: Artificial Sequence
<220> FEATURE:
<223> OTHER INFORMATION: Oligonucleotide used for chip attachment

<400> SEQUENCE: 8
catcgtcctt gtagtc                                              16

<210> SEQ ID NO 9
<211> LENGTH: 13
<212> TYPE: DNA
<213> ORGANISM: Artificial Sequence
<220> FEATURE:
<223> OTHER INFORMATION: Oligonucleotide used for chip attachment

<400> SEQUENCE: 9
cgtcgtaggg gta                                                 13
```

```
<210> SEQ ID NO 10
<211> LENGTH: 14
<212> TYPE: DNA
<213> ORGANISM: Artificial Sequence
<220> FEATURE:
<223> OTHER INFORMATION: Oligonucleotide used for chip attachment

<400> SEQUENCE: 10
ccgctcctga tgta                                                        14

<210> SEQ ID NO 11
<211> LENGTH: 13
<212> TYPE: DNA
<213> ORGANISM: Artificial Sequence
<220> FEATURE:
<223> OTHER INFORMATION: Oligonucleotide used for chip attachment

<400> SEQUENCE: 11
tcgggaggca ttg                                                         13

<210> SEQ ID NO 12
<211> LENGTH: 99
<212> TYPE: DNA
<213> ORGANISM: Artificial Sequence
<220> FEATURE:
<223> OTHER INFORMATION: FLAG amplification sequence

<400> SEQUENCE: 12
taatacgact cactataggg acaattacta tttacaatta caatggacta caaggacgat      60
gacgataagg gcggctggtc caccccag ttcgagaag                               99

<210> SEQ ID NO 13
<211> LENGTH: 102
<212> TYPE: DNA
<213> ORGANISM: Artificial Sequence
<220> FEATURE:
<223> OTHER INFORMATION: HA11 amplification sequence

<400> SEQUENCE: 13
taatacgact cactataggg acaattacta tttacaatta caatgtaccc ctacgacgtg      60
cccgactacg ccggcggctg gtcccacccc cagttcgaga ag                        102

<210> SEQ ID NO 14
<211> LENGTH: 39
<212> TYPE: DNA
<213> ORGANISM: Artificial Sequence
<220> FEATURE:
<223> OTHER INFORMATION: Oligonucleotide used for PCR

<400> SEQUENCE: 14
taatacgact cactataggg acaattacta tttacaatt                             39

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide used for PCR

<400> SEQUENCE: 15
agcggatgcc ttctcgaact gggggtggga                                       30

<210> SEQ ID NO 16
<211> LENGTH: 32
<212> TYPE: DNA
```

```
<213> ORGANISM: Artificial Sequence
<220> FEATURE:
<223> OTHER INFORMATION: Oligonucleotide used as a splint containing
      biotin moiety at 5' terminus

<400> SEQUENCE: 16
tgcaacgacc aacttttttt tttagcgcat gc                                    32

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide used as a splint containing
      mbiotin moiety at 5' terminus
<220> FEATURE:
<221> NAME/KEY: variation
<222> LOCATION: (23)...(23)
<223> OTHER INFORMATION: n is a, c, t, or g.

<400> SEQUENCE: 17
tgcaacgacc aactttttttt ttnagcgcat gc                                   32

<210> SEQ ID NO 18
<211> LENGTH: 31
<212> TYPE: DNA
<213> ORGANISM: Artificial Sequence
<220> FEATURE:
<223> OTHER INFORMATION: Oligonucleotide used for elution displacement

<400> SEQUENCE: 18
gcatccgcta aaaaaaaaag ttggtcgttg c                                     31

<210> SEQ ID NO 19
<211> LENGTH: 169
<212> TYPE: RNA
<213> ORGANISM: Artificial Sequence
<220> FEATURE:
<223> OTHER INFORMATION: Oligonucleotide used to make c-myc fusion

<400> SEQUENCE: 19
uaauacgacu cacuauaggg acaauuacua uuuacaauua caaugggac aauuacuauu        60 uacaauuaca auggcugaag aacagaaacu gaucucugaa gaagaccugc ugcguaaacg      120
ucgugaacag cugaaacaca aacuggaaca gcugcguaac ucuugcgcu                  169

<210> SEQ ID NO 20
<211> LENGTH: 20
<212> TYPE: DNA
<213> ORGANISM: Artificial Sequence
<220> FEATURE:
<223> OTHER INFORMATION: Capture probe sequence

<400> SEQUENCE: 20
ttgtaaatag taattgtccc                                                  20

<210> SEQ ID NO 21
<211> LENGTH: 20
<212> TYPE: DNA
<213> ORGANISM: Artificial Sequence
<220> FEATURE:
<223> OTHER INFORMATION: Capture probe sequence

<400> SEQUENCE: 21
agagatcagt ttctgttctt                                                  20
```

```
<210> SEQ ID NO 22
<211> LENGTH: 20
<212> TYPE: DNA
<213> ORGANISM: Artificial Sequence
<220> FEATURE:
<223> OTHER INFORMATION: Capture probe sequence

<400> SEQUENCE: 22
agtttgtgtt tcagctgttc                                              20

<210> SEQ ID NO 23
<211> LENGTH: 25
<212> TYPE: DNA
<213> ORGANISM: Artificial Sequence
<220> FEATURE:
<223> OTHER INFORMATION: Capture probe sequence

<400> SEQUENCE: 23
tttttttttt tttttttttt ttttt                                        25

<210> SEQ ID NO 24
<211> LENGTH: 20
<212> TYPE: DNA
<213> ORGANISM: Artificial Sequence
<220> FEATURE:
<223> OTHER INFORMATION: Capture probe sequence

<400> SEQUENCE: 24
agagatctca atctgttctt                                              20

<210> SEQ ID NO 25
<211> LENGTH: 20
<212> TYPE: DNA
<213> ORGANISM: Artificial Sequence
<220> FEATURE:
<223> OTHER INFORMATION: Capture probe sequence

<400> SEQUENCE: 25
ttcttgtctt tgactagaga                                              20

<210> SEQ ID NO 26
<211> LENGTH: 99
<212> TYPE: DNA
<213> ORGANISM: Artificial Sequence
<220> FEATURE:
<223> OTHER INFORMATION: c-myc epitope amplification sequence

<400> SEQUENCE: 26
agcgcaagag ttacgcagct gttccagttt gtgtttcagc tgttcacgac gtttacgcag    60
caggtcttct tcagagatca gtttctgttc ttcagccat                           99

<210> SEQ ID NO 27
<211> LENGTH: 21
<212> TYPE: DNA
<213> ORGANISM: Artificial Sequence
<220> FEATURE:
<223> OTHER INFORMATION: Oligonucleotide used for PCR

<400> SEQUENCE: 27
agcgcaagag ttacgcagct g                                            21

<210> SEQ ID NO 28
<211> LENGTH: 62
<212> TYPE: DNA
<213> ORGANISM: Artificial Sequence
<220> FEATURE:
```

```
<223> OTHER INFORMATION: Oligonucleotide used for PCR

<400> SEQUENCE: 28
taatacgact cactataggg acaattacta tttacaatta caatggctga agaacagaaa      60
ct                                                                     62

<210> SEQ ID NO 29
<211> LENGTH: 19
<212> TYPE: DNA
<213> ORGANISM: Artificial Sequence
<220> FEATURE:
<223> OTHER INFORMATION: Oligonucleotide used as a splint

<400> SEQUENCE: 29
tttttttttt agcgcaaga                                                   19
```

ADDRESSABLE PROTEIN ARRAYS

This application claims the benefit of the filing date of U.S. provisional application, U.S. Ser. No. 60/080,686, filed Apr. 3, 1998.

BACKGROUND OF THE INVENTION

The invention relates to fixed arrays of nucleic acid-protein fusions and, in particular, RNA-protein fusions, on solid supports.

Certain macromolecules, such as proteins, are known to interact specifically with other molecules based on the three-dimensional shapes and electronic distributions of those molecules. For example, proteins interact selectively with other proteins, with nucleic acids, and with small-molecules. Modern pharmaceutical research relies on the study of these interactions; the development of new drugs depends on the discovery of compounds that bind specifically to biologically important molecules.

The discovery of a single drug candidate can require the screening of thousands of compounds. It is therefore important to be able to screen large numbers of compounds rapidly and efficiently. One method for screening a large number of compounds is to fix possible binding partners, such as proteins, to a solid support.

It is difficult to prepare arrays of isolated proteins on solid supports, however, for a variety of reasons. First of all, proteins cannot always be easily attached to the planar surfaces traditionally used to make other fixed arrays, such as nucleic acid microchips. More importantly, because proteins can interact with the functional groups on the surfaces of these supports, the proximity of the protein to the surface can lead to disruption of the protein structure.

SUMMARY OF THE INVENTION

In general, the invention features a solid support including an array of immobilized capture probes; each of the capture probes includes a non-nucleosidic spacer group and an oligonucleotide sequence to which a nucleic acid-protein fusion is bound (for example, hybridized or covalently bound). In preferred embodiments, the nucleic acid-protein fusion is an RNA-protein fusion, and the protein component is encoded by the nucleic acid (for example, the RNA). The spacer group can include a polyalkylene oxide, for example, polyethylene oxide. A preferred spacer group includes hexa-ethylene oxide. The capture probe may also include a photocleavable linker.

The oligonucleotide sequence can include a modified base, such as 5-propyne pyrimidine. It can also include an internucleotide analog (such as 3'-phosphoramidate) or a carbohydrate modification (such as a 2'-O-methyl group). The nucleic acid-protein fusion can include a hybridization tag sequence. The hybridization tag sequence can also include a modified base, an internucleotide analog, or a carbohydrate modification.

In a preferred embodiment, the capture probe further includes a reactive moiety (for example, a nucleophilic group), such as a primary amino group. In another preferred embodiment, the nucleic acid-protein fusion is covalently linked to the capture probe (for example, by photo-crosslinking); in one preferred approach, this is accomplished by including one or more psoralen moieties in the capture probe or in the capture probe-fusion hybridization reaction mixture. A preferred solid support is a glass or silica-based chip.

In a related aspect, the invention features a solid support including an array of immobilized capture probes; each of the capture probes is attached to the surface of the solid support through a non-nucleosidic spacer group, and each of the capture probes includes an oligonucleotide sequence to which a nucleic acid-protein fusion (for example, an RNA-protein fusion) is bound (for example, hybridized or covalently bound).

In another related aspect, the invention features a solid support including an array of immobilized capture probes; each of the capture probes includes a non-nucleosidic spacer group and an oligonucleotide sequence to which a ribosome display particle is bound (for example, hybridized or covalently bound).

In yet another related aspect, the invention features a method for preparing a solid support. The method includes the steps of: (a) preparing a capture probe by linking a spacer group to an oligonucleotide sequence; (b) attaching the capture probe to the solid support; and (c) binding (for example, hybridizing or covalently binding) a nucleic acid-protein fusion (for example, an RNA-protein fusion) to the capture probe.

The invention also features a second general method for preparing a solid support. This method includes the steps of: (a) attaching a spacer group to a surface of the solid support; (b) attaching a bifunctional linker to the spacer group; (c) attaching a capture probe to the bifunctional linker; and (d) binding (for example, hybridizing or covalently binding) a nucleic acid-protein fusion (for example, an RNA-protein fusion) to the capture probe.

In a second aspect, the invention features a method for detecting an interaction between a protein and a compound. The method includes the steps of: (a) providing a solid support including an array of immobilized capture probes, where each of the capture probes includes a non-nucleosidic spacer group and an oligonucleotide sequence to which a nucleic acid-protein fusion is bound (for example, hybridized or covalently bound); (b) contacting the solid support with a candidate compound under conditions which allow an interaction between the protein portion of the nucleic acid-protein fusion and the compound; and (c) analyzing the solid support for the presence of the compound as an indication of an interaction between the protein and the compound.

Alternatively, the invention features another method for detecting an interaction between a protein and a compound; this method involves the steps of: (a) providing a population of nucleic acid-protein fusions; (b) contacting the population of nucleic acid-protein fusions with a candidate compound under conditions which allow an interaction between the protein portion of the nucleic acid-protein fusion and the compound; (c) contacting the product of step (b) with a solid support that includes an array of immobilized capture probes, each of the capture probes including a non-nucleosidic spacer group and an oligonucleotide sequence to which a nucleic acid-protein fusion binds (for example, hybridizes or covalently binds); and (d) analyzing the solid support for the presence of the compound as an indication of an interaction between the protein and the compound.

In a preferred embodiment of each of the above methods, the nucleic acid-protein fusion is an RNA-protein fusion. In another preferred embodiment, the compound is labeled. Compounds that can be screened using these methods include, without limitation, proteins, drugs, therapeutics, enzymes, and nucleic acids.

In a third aspect, the invention features an array (for example, an addressable array) of nucleic acid-protein fusions including at least $10^2$ different fusions/cm$^2$. Preferably, the nucleic acid-protein fusions are RNA-protein fusions, and the array includes at least $10^4$ different fusions/cm$^2$.

In a related aspect, the invention features a method for generating an addressable array of molecules. The method involves: (a) providing a solid support on which an array of nucleic acid molecules is immobilized; (b) contacting the solid support with a population of addressable molecules; and (c) allowing the addressable molecules to orient themselves on the solid support by sequence-dependent recognition and binding of the immobilized nucleic acid molecules.

In preferred embodiments of this method, the addressable array of molecules is an array of nucleic acid-protein fusions (for example, an array of RNA-protein fusions); the addressable molecules orient themselves on the solid support by base pairing (for example, hybridization) with the immobilized nucleic acid molecules; the solid support is a glass or silica-based chip; and the nucleic acid molecules immobilized on the solid support are capture probes, each including a non-nucleosidic spacer group and an oligonucleotide sequence to which the addressable molecule binds.

As used herein, by an "array" is meant a fixed pattern of immobilized objects on a solid surface or membrane. Typically, the array is made up of nucleic acid-protein fusion molecules (for example, RNA-protein fusion molecules) bound to capture nucleic acid sequences which themselves are immobilized on the solid surface or membrane. The array preferably includes at least $10^2$, more preferably at least $10^3$, and most preferably at least $10^4$ different fusions, and these fusions are preferably arrayed on a 125×80 mm, and more preferably on a 10×10 mm, surface. By an "addressable array" is meant that the locations, or addresses, on the solid support of the members of the array (for example, the nucleic acid-protein fusions) are known; the members of the array are referred to as "addressable molecules" and are utilized in methods for screening for subsequent molecular interactions (for example, for screening for interactions between the addressable nucleic acid-protein fusions and candidate therapeutics).

By "nucleic acid-protein fusion" is meant a nucleic acid covalently bound to a protein. By "nucleic acid" is meant any two or more covalently bonded nucleotides or nucleotide analogs or derivatives. As used herein, this term includes, without limitation, DNA, RNA, and PNA. By "protein" is meant any two or more amino acids, or amino acid analogs or derivatives, joined by peptide or peptoid bond(s), regardless of length or post-translational modification. As used herein, this term includes, without limitation, proteins, peptides, and polypeptides.

By "hybridization tag" is meant a non-coding oligonucleotide sequence that differs sufficiently in sequence from other nucleic acid sequences in a given population or reaction mixture that significant cross-hybridization does not occur. When multiple hybridization tags are utilized in a single reaction mixture, these tags also preferably differ in sequence from one another such that each has a unique binding partner under the conditions employed.

By a "population" is meant more than one molecule.

By a "solid support" is meant any solid surface including, without limitation, any chip (for example, silica-based, glass, or gold chip), glass slide, membrane, bead, solid particle (for example, agarose, sepharose, or magnetic bead), column (or column material), test tube, or microtiter dish.

BRIEF DESCRIPTION OF THE DRAWINGS

FIG. 6 is a schematic diagram of the layout of the Myc fusion chip capture probes utilized in FIGS. 7 and 8. In this Figure, capture probes CP01, CP33, CP80, CP125, CPmm, and CPns (described herein) were arranged on the chip as follows: CP01 at locations A1, B1, C1, A4, B4, and C4; CP33 at locations D1, E1, F1, D4, E4, and F4; CP80 at locations A2, B2, C2, A5, B5, and C5; CP125 at locations D2, E2, F2, D5, E5, and F5; CPmm at locations A3, B3, C3, A6, B6, and C6; and CPns at locations D3, E3, F3, D6, E6, and F6.

DESCRIPTION OF THE PREFERRED EMBODIMENTS

The invention features support-based, addressable arrays of proteins, and methods for preparing and using these arrays. The arrays are prepared by fixing oligonucleotide sequences, the capture probes (or capture oligos), to a support in a defined array. The capture probes are then used to bind nucleic acid-protein fusions, such as RNA-protein fusions. Such binding may occur through base pairing (for example, through Watson-Crick base pairing, pseudo Watson-Crick base pairing involving modified bases, or Hoogsteen base pairing) between the nucleic acid component of the fusion and a complementary capture probe, or may occur through any other type of sequence-dependent recognition and binding of the capture probe (including, without limitation, polyamide-mediated nucleic acid groove binding or specific binding by nucleic acid-binding proteins such as transcription factors). The result of the binding interactions between the fusions and the capture probes is a defined, addressable array of proteins attached to a solid support.

A variety of materials can be used as the solid support. Examples of such materials include polymers (e.g., plastics), aminated surfaces, gold coated surfaces, nylon membranes, polyacrylamide pads deposited on solid surfaces, silicon, silicon-glass (e.g., microchips), silicon wafers, and glass (e.g., microscope slides). Microchips, and particularly glass microchips, represent a preferred solid support surface.

Figure 1:
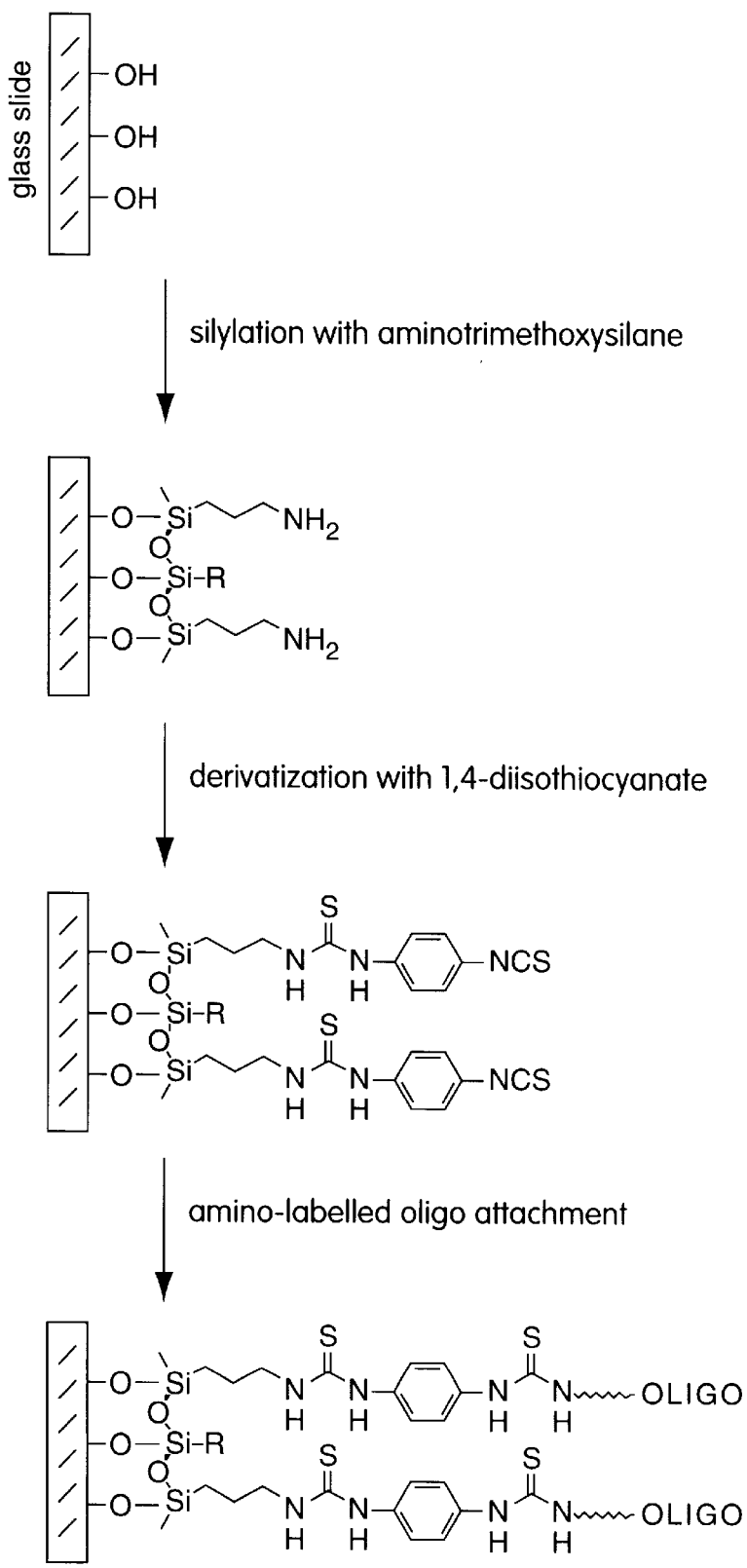
FIG. 1 is a drawing showing the silylation of a glass surface, the derivatization of the resulting amino groups, and the attachment of a capture probe to the modified surface.

If the surface is not already aminated, it can be modified to provide a layer of amino groups. For example, a glass microscope slide can be treated with a silylating agent such as trialkoxyaminosilane to provide a surface of primary amino groups that exists as a monolayer or 3–8 molecular layers. This reaction is illustrated in FIG. 1. The silane-treated surface is then derivatized with a homobifunctional or heterobifunctional linker that permits the attachment of oligonucleotides at discrete positions. Phenylene 1,4-diisothiocyanate is a useful homobifunctional linker; amino-surfaces derivatized with this reagent have isothiocyanate functionalities that are available to covalently react with the primary amino groups on the termini of oligonucleotides to form stable thiourea bonds, as shown in FIG. 1.

The capture probes, i.e., the oligonucleotide sequences that are to be attached to the surface, are selected from the reverse-complements of the nucleic acid components of the nucleic acid-protein fusions (the targets). Capture probes preferably have between 5 and 30 nucleotide units, and more preferably have about 20 nucleotide units. Considerations for the selection of the exact sequence for a particular capture probe include melting temperature (Tm), interference from competing target sequences, and potential secondary structure in the target sequence. Ideally, each unique capture probe has the same Tm, i.e., they are isoenergetic, so a single hybridization and washing temperature can be used successfully for all capture-target pairs. Commercially available computer programs (e.g., Oligo 4.0) can be used to help identify sets of capture probes with similar thermodynamic properties based on nearest neighbor treatments.

Figure 2:
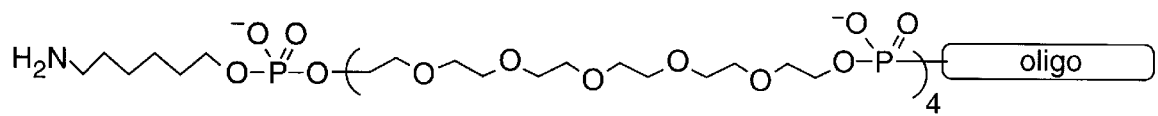
FIG. 2 is a drawing illustrating a capture probe containing a non-nucleosidic spacer group and a reactive moiety.

The capture probes are modified before they are attached to the surface. One or more non-nucleosidic spacers, such as polyethylene oxide, are added to the terminus of the oligo. Preferably, 1–20 spacers and, most preferably, 4 spacers are utilized. These spacers may be added to either the 5' or preferably the 3' end of the oligonucleotide. A nucleophilic moiety is then attached to the spacer group. The result is a derivatized capture probe, as shown in FIG. 2. A preferred spacer monomer includes hexaethylene oxide.

Non-nucleosidic spacers are preferred over nucleosidic spacers, such as poly-T, because non-nucleosidic spacers have greater flexibility. In addition, their physical properties can be tailored relatively easily, and it is possible to minimize specific and non-specific nucleic acid interactions.

The spacers provide physical separation between the oligonucleotide and the solid surface and prevent interaction of the proteins with the support surface. This separation is important to ensure effective hybridization between the support-bound capture probe and the nucleic acid-protein fusion. In addition, the separation helps to minimize denaturation of the protein; the proteins are therefore able to adopt their native folded structures and remain functional.

Alternatively, the spacer groups can be attached directly to the solid support surface, instead of to the capture probes. For example, the spacer group can be attached to the amino groups on the surface. The bifunctional linker can then be attached to the other end of the spacer group.

In addition to spacer groups, the capture probes may contain modifications that improve their hybridization properties and mismatch discrimination. For example, they may contain base analogs, such as 5-propyne pyrimidines, internucleotide analogues such as peptide nucleic acids (PNA), in which the bases are connected by peptide-like linkages, or carbohydrate modifications.

The capture probes are suspended in an aqueous alkaline solution, then applied to defined positions of the support surface; the nucleophilic moieties at the termini of the capture probes react with the active sites of the bifunctional linkers to form covalent bonds. The density of the capture probes can be controlled by adjusting reaction time and oligo concentration. Alternatively, the density can be controlled by doping the solution with capture oligos that lack nucleophilic moieties or doping with simple organic compounds that possess amine functional groups.

The capture probes can be applied using liquid deposition techniques, such as inkjet delivery, robotic quill delivery or spotting, and other similar deposition methods. They can also be applied using manual methods, such as pipetting. The feature sizes of the capture probes can range from one square micron (e.g., when robotic techniques are used) to one square millimeter (e.g., when a 0.2 microliter pipette is used). The result of the application of the capture probes is a defined, regular array of nucleic acid sequences.

After a sufficient reaction time, the excess capture probe is washed away, and the remaining unreacted isothiocyanate groups are blocked off. Dilute ammonia can be used as the blocking agent, resulting in a surface of phenyl thiourea groups. Blocking agents can also be selected to modify the surface energy, i.e., the hydrophobicity of the solid support surface. The hydrophobicity of the solid support surface is important because it affects the background signal level and the extent of unwanted interaction of the protein portion of a nucleic acid-protein fusion with the surface. Examples of blocking agents that modify hydrophobicity are methylamine, amino alcohols, and suitable amino-containing polyethylene oxide moieties.

Non-covalent blocking agents can also be used to further minimize non-specific interactions between the fusion and the solid support (e.g., glass) surface. Examples of such blocking agents include non-specific proteins such as BSA or casein, or similar commercially available blocking reagent formulations marketed for use with membranes.

The capture probes arrayed on the surface of the solid support are then bound (for example, by hybridization) to nucleic acid-protein fusions, such as RNA-protein fusions. A solution containing the mixture of fusions is adjusted to an appropriate salt concentration, applied to the surface, and incubated at a suitable temperature to allow for efficient binding (for example, hybridization) between the capture probe and the target sequence. The solution may also contain surfactants such as TWEEN-20, TRITON X-100, or SDS (Sigma Chemical Co.) at concentrations of about 0.02% to about 1.0%; it may also include non-specific proteins, such as BSA.

The experimental variables of salt concentration, temperature, and hybridization time are a function of the capture oligo design. A preferred range for the salt concentration is 25 mM to 2 M, with a concentration of about 750 mM being especially preferred. A preferred temperature range is from 5° C. to 70° C., with 30° C. being especially preferred. Preferred reaction times can be from 1 to 24 hours, with 3 hours being especially preferred. The variables for each experiment are determined empirically by standard methods. The hybridization step can be performed in a simple chamber device that constrains the liquid sample and prevents evaporation.

When RNA-protein fusions are utilized as addressable arrays, the solution may also contain one or more components to suppress nuclease degradation of the RNA moiety. Preferred additions include (a) metal chelators (e.g., EDTA or EGTA) at concentrations of between 1–10 mM, (b) placental RNase inhibitor protein (Promega) at concentrations of between 0.1–1 Unit/$\mu$l; and (c) Anti-RNase protein (Ambion) at concentrations of between 0.1–1 Unit/$\mu$l. A separate strategy to specifically suppress 5'-exonuclease degradation involves capping the 5'-terminus of the fusion RNA with a binding molecule. The capping strategy may be used in conjunction with one or more of the components listed above. In one particular capping approach, a native or analog (e.g., PNA) nucleic acid sequence complementary the 5'-terminus of the fusion RNA is added to generate a stable duplex at the 5'-end. The complementary sequence is preferably between 10–50 bases in length, and most preferably about 20 bases in length. This added nucleic acid sequence may also contain pendant groove-binding, intercalating, or cross-linking moieties. Alternatively, native or analog nucleic acid sequences may be added that form stable intermolecular hairpin, tetraloop, or pseudoknot secondary structures with the 5'-terminus of the RNA. In the latter case, these nucleic acids are preferably about 20–100 bases in length, with about 35 bases being especially preferred.

To the extent possible, the mixture of nucleic acid-protein fusions should be free of un-fused nucleic acids. Un-fused nucleic acids that are complementary to the capture probes will compete with the fusions for binding and will limit the amount of a given protein that can be displayed on the solid support. Preferably, at least 1% of the nucleic acid (for example, the RNA message) is fused to protein.

Unique non-coding regions can be incorporated into the nucleic acid component of the fusion for the specific purpose of being "captured" by the capture probe; these non-coding regions are referred to as "hybridization tag sequences." The hybridization tag sequences may include the same analogue units as are described above for the capture probes. In some cases, both the capture probe and the tag sequences can be modified so they hybridize preferentially with each other, thereby minimizing interference from the coding fusion sequences.

Upon completion of the binding step, unbound nucleic acid-protein fusion is washed away with a buffer that has a higher stringency and a lower salt concentration than that used for the hybridization step. Again, the optimal buffer composition is determined empirically by standard methods. What remains upon completion of washing is an addressable array of proteins on the solid surface, attached via sequence-dependent recognition between the nucleic acid component of the fusion and the surface-bound capture oligo. The position of each protein is defined, because each fusion corresponds to the complementary capture probe.

In addition, if desired, the nucleic acid component of the fusion may be covalently linked to a part of the solid support, the linker, or the capture probe. Such covalently linked fusions provide particularly robust and versatile addressable arrays that may be used, for example, in the screening methods described herein. Covalently linked fusion arrays may be generated by any standard approach. According to one general technique, the fusions are addressed to specific locations on a solid surface via hybridization with corresponding capture probes, and a chemical cross-linking or attachment reaction is triggered to fix the location of the fusions on the solid support. One method to achieve such a covalent link involves functionalizing the DNA capture oligos during chemical synthesis with one or more pendant psoralen moieties, preferably positioned near adenosine bases. After hybridizing the nucleic acid-protein fusion (for example, the RNA-protein fusion) to the support-bound capture oligos, the surface is exposed to long-wavelength UV light (for example, at 350 nm). Light of this wavelength triggers a photoreaction between psoralen and an adjacent thymidine or uridine base in the duplex region, forming a cyclobutane linkage and permanently attaching the fusion to the solid support. Alternatively, psoralen itself (i.e., not linked to a capture probe) may be included in the hybridization solution or in a subsequent separate solution. The psoralen molecule intercalates between bases in double-stranded regions. Upon irradiation with long-wavelength UV light, the intercalated psoralen cross-links with thymidine or uridine bases (intrastrand and interstrand) in a bifunctional mode, forming covalent links between the capture probe and the nucleic acid component of the fusion. Other reactive, cross-linking reagents may also be used in place of psoralen in combination with triggering conditions appropriate for those reagents.

Ordered, addressable arrays of peptide fragments can also be prepared. To prepare these arrays, the fusion library is generated from short synthetic DNA sequences or fragments of cDNAs or genomic DNAs. In another variation, ribosome display particles, such as those described in Gold et al., WO 93/03172, can be hybridized to the solid support to generate the protein array. Again, these particles are immobilized on the solid support through a hybridization reaction between the capture oligo and the protein-coding RNA.

Use

The addressable protein arrays of the present invention have many uses. For example, a library of proteins can be displayed on a support, such as a microchip. This microchip can then be used to identify previously unknown protein-protein interactions. A probe protein can be detectably labeled, for example, with a radioisotope, chromophore, fluorophore, or chemiluminescent species, then incubated with the microchip. After the excess probe protein is washed away, the chip surface is analyzed for signal from the label. Detection of a signal indicates interaction of the labeled protein with one or more unique members of the protein library. The identity of proteins that are able to bind to the probe protein can then be determined from the location of the spots on the chip that become labeled due to binding of the probe. The same approach can also be used to screen protein libraries for protein-ligand interactions and protein-nucleic acid interactions.

Other methods can be used to detect protein-protein, protein-ligand, or protein-nucleic acid interactions. For example, when the solid surface used to form the protein array is a gold layer, surface plasmon resonance (SPR) can be used to detect mass changes at the surface. When gold surfaces are employed, the reactive moiety on the oligonucleotide capture probe is a thiol group (rather than an amino group) and the gold surface need not be functionalized to achieve capture probe attachment. Mass spectrometry (especially, MALDI-TOF) can also be used to analyze species bound to unique members of the protein library.

Another application of protein arrays is the rapid determination of proteins that are chemically modified through the action of modifying enzymes such as protein kinases, acyl transferases, and methyl transferases. By incubating the protein array with the enzyme of interest and a radioactively labeled substrate, followed by washing and autoradiography, the location and hence the identity of those proteins that are substrates for the modifying enzyme may be readily determined. Further localization of the modification sites can be achieved using ordered displays of fragments of these proteins.

The protein arrays can also be used to identify the unknown protein targets of therapeutically active compounds. For example, a therapeutic compound may be applied to a protein array derived from cellular RNA. Detection of the captured therapeutic compound, either through its bound label or directly (for example, by mass spectrometry or surface plasmon resonance) reveals the compound's binding partner or partners. In addition, arrays can also be used in the development of protein-based diagnostics. For example, a solid support containing a variety of proteins associated with various illnesses can be prepared. A single patient sample, which might contain one or more proteins whose interactions with the support-bound proteins would be indicative of certain illnesses, can then be contacted with the support. Thus, a single sample can be used to simultaneously detect the presence of several conditions, or to distinguish between conditions. Alternatively, addressable arrays may be used to quantify target molecules in a sample. In one particular example, addressable arrays of single chain antibodies or antibody mimics may be used for quantifying a target protein (or proteins) in a biological sample. The arrays can also be used in the emerging fields of proteomics and functional genomics.

The specific fusions that are identified as binding specifically to a probe molecule can be removed from the support surface. In one method, the fusion is released by disrupting hybridization with the capture probe. In one particular approach, the specified fusion is physically separated from the rest of the fusions, then treated with a denaturing agent, such as a chemical reagent or heat, to disrupt the base pairing with the capture oligo. The liberated fusion is then recovered from the solution.

Alternatively, the entire capture probe can be detached. During solid support preparation, a light-sensitive linker can be used to attach the capture probe to the solid surface. Following identification of the active fusion, a laser beam of the appropriate wavelength can be used to cleave the linker, thus releasing the desired fusion. Following release from the surface by any of the above methods, the fusion can be specifically recovered and manipulated, for example, using PCR, and further characterized.

There now follow particular examples of the preparation of protein arrays according to the invention. These examples are provided for the purpose of illustrating the invention, and should not be construed as limiting.

EXAMPLE 1

Silylation of a Glass Surface

Select grade, low-iron content, pre-cleaned 1×3 inch glass microscope slides (VWR Scientific) are prepared by heating with 1 M hydrochloric or nitric acid for 30 minutes at 70° C. The slides are then subjected to three 5-minutes washes, using fresh distilled water for each wash. A 1% solution of aminopropyltrimethoxysilane (Gelest, Inc.) in 95% acetone/5% water is prepared and allowed to hydrolyze for at least five minutes. The glass slides are immersed in the hydrolyzed silane solution for 2–20 minutes with gentle agitation. Excess silane is removed by subjecting the slides to ten 5-minute washes, using fresh portions of 95% acetone/5% water for each wash, using gentle agitation. The slides are then cured by heating at 110° C. for 20–45 minutes.

EXAMPLE 2

Derivatization with a Homobifunctional Linker

Silane treated slides from Example 1 are immersed in a freshly prepared 0.2% solution of phenylene 1,4-diisothiocyanate (Aldrich Chemical Co.) in 90% DMF/10% pyridine for two hours, with gentle agitation. The slides are washed sequentially with 90% DMF/10% pyridine, methanol, and acetone. After air drying the functionalized slides are stored at 0° C. in a vacuum desiccator over anhydrous calcium sulfate.

EXAMPLE 3

Synthesis of Capture Probes

Oligonucleotides are chemically synthesized in the 3'→5' direction by coupling standard phosphoramidite monomers with an automated DNA synthesizer. Typically, 500 angstrom controlled-pore glass supports are used at the 0.2 micromole scale. After the desired probe sequence has been assembled (using A, G, C, and T monomers), hexaethylene oxide phosphoramidite monomer (Glen Research) is added to the 5' terminus. The coupling wait time is extended to 15 minutes by modifying the synthesizer program. Additional hexaethylene oxide monomer units are added in the same way. C-6 Amino phosphoramidite (Glen Research) is then added to the 5' terminus; the coupling wait time is again extended to 15 minutes. The acetic anhydride capping step and the final acidic detritylation step are eliminated. Capture probe sequences are cleaved from the solid support and deprotected with ammonium hydroxide, concentrated to dryness, precipitated in ethanol, and purified by reverse-phase HPLC using an acetonitrile gradient in triethylammonium acetate buffer.

EXAMPLE 4

Attachment of Capture Probes

The purified, amine-labeled capture probes from Example 3 are adjusted to a concentration of 500 micromolar in 100 mM sodium carbonate buffer (pH 9.0), and are applied to the derivatized glass surface from Example 2 at defined positions. For manual deposition, aliquots of 0.2 microliter each are applied with a pipetman. The array is incubated at room temperature in a moisture-saturated environment for at least two hours. The attachment reaction is terminated by immersing the glass surface in an aqueous 1% ammonia solution for five minutes with gentle agitation. The glass surface is then subjected to three 5-minute washes, using fresh portions of distilled water for each wash. The array is then soaked in 1 M phosphate buffered saline (PBS) solution for 2 hours at room temperature, then rinsed again for 5 minutes in distilled water.

EXAMPLE 5

Surface Modification

The ammonia solution from Example 4 is replaced with a 1–5% aqueous solution of a different primary amine-containing molecule. A small amount (10%) of methanol or acetonitrile cosolvent is added, if necessary.

The glass surface is then subjected to three 5-minute washes, using fresh portions of distilled water for each wash. The surface is soaked in 1 M phosphate buffered saline (PBS) solution for 2 hours, then washed again for 5 minutes with distilled water. The glass surface is immersed in a dilute, aqueous solution of a protein-containing blocking solution for several minutes, then subjected to three 5-minute washes, using fresh portions of distilled water for each wash. Finally, the surface is air dried.

EXAMPLE 6

Fusion Hybridization 50 microliters of a solution containing the RNA-protein fusions and consisting of 25 mM Tris-HCl (pH 8.0) and 100 mM potassium chloride are applied to the glass microchip surface in a chamber that can contain and seal the liquid. The solution is maintained at a specific temperature (determined by the capture oligo design) for at least three hours. Excess, non-hybridized RNA-protein fusions are removed by washing with 25 mM Tris-HCl (pH 8.0) and 50 mM potassium chloride for several minutes at the incubation temperature. The protein chip is subjected to two 15-minute washes, using a buffer that is more stringent and contains a lower salt concentration than the buffer used for the hybridization reaction.

EXAMPLE 7

Generation of an Exemplary FLAG and HA11 Fusion Chip

Using the techniques essentially as described above, exemplary FLAG and HA11 fusion chips were generated as follows.

For silylation of the glass microchip surface, pre-cleaned 1×3 inch glass microscope slides (Goldseal, #3010) were treated with Nanostrip (Cyantek) for 15 minutes, 10% aqueous NaOH at 70° C. for 3 minutes, and 1% aqueous HCl for 1 minute, thoroughly rinsing with deionized water after each solution. The slides were then dried in a vacuum desiccator over anhydrous calcium sulfate for several hours. A 1% solution of aminopropytrimethoxysilane (Gelest, Inc.) in 95% acetone/5% water was prepared and allowed to hydrolyze for 20 minutes. The glass slides were immersed in the hydrolyzed silane solution for 5 minutes with gentle agitation. Excess silane was removed by subjecting the slides to ten 5-minute washes, using fresh portions of 95% acetone/5% water for each wash, with gentle agitation. The slides were then cured by heating at 110° C. for 20 minutes.

To derivatize with a homobifunctional linker, the silane treated slides were immersed in a freshly prepared 0.2% solution of phenylene 1,4-diisothiocyanate (Aldrich Chemical Co.) in 90% DMF/10% pyridine for two hours, with gentle agitation. The slides were washed sequentially with 90% DMF/10% pyridine, methanol, and acetone. After air drying, the functionalized slides were stored at 0° C. in a vacuum desiccator over anhydrous calcium sulfate.

Capture oligos were then designed and synthesized by standard techniques. In particular, the RNA employed to make the FLAG epitope fusion (17 amino acids total) consisted of 5'-r(UAA UAC GAC UCA CUA UAG GGA CAA UUA CUA UUU ACA AUU ACA AUG GAC UAC AAG GAC GAU GAC GAU AAG GGC GGC UGG UCC CAC CCC CAG UUC GAG AAG) (SEQ ID NO: 1). The RNA employed to make the HA11 epitope fusion (20 amino acids total) consisted of 5'-r(UAA UAC GAC UCA CUA UAG GGA CAA UUA CUA UUU ACA AUU ACA AUG UAC CCC UAC GAC GUG CCC GAC UAC GCC GGC GGC UGG UCC CAC CCC CAG UUC GAG AAG) (SEQ ID NO: 2). In addition, in each case, the following DNA linker, which also contained the essential puromycin moiety at its 3'-end, was ligated to the 3'-terminus of the RNA message: 5'-d(AAAAAAAAAAAAAAAAAAAAAAAAAAACC) (SEQ ID NO: 3).

Specific, non-interacting, and thermodynamically isoenergetic sequences along the target RNAs were identified to serve as capture points. The software program HybSimulator v2.2 (Advanced Gene Computing Technology, Inc.) facilitated the identifcation and analysis of potential capture probes. A single specific capture probe for each RNA was ultimately identified (CPflag and CPha11). In addition, two sequences common to each RNA (CPt7, CPtag) were also identified to serve as positive controls. Four non-sense sequences (CPau1, CPau5, CPirs, CPkt3) were generated as well to serve as negative controls. In total, eight unique sequences were selected. These oligonucleotides were prepared so that they could be attached to the chip surface at either the 3'- or 5'-terminus. Therefore, 16 capture probes were prepared comprising eight unique sequences. The following is a list of these capture probe sequences (5' to 3') (SEQ ID NOS: 4–11):

CPt7: TGTAAATAGTAATTGTCCC
CPtag: CTTCTCGAACTGGG
CPau 1: CCTGTAGGTGTCCAT
CPau5: CAGGTAGAAGTCGGT
CPflag: CATCGTCCTTGTAGTC
CPha11: CGTCGTAGGGGTA
CPirs: CCGCTCCTGATGTA
CPkt3: TCGGGAGGCATTG.

Oligonucleotide capture probes were chemically synthesized in the 3' to 5' direction by coupling standard phosphoramidite monomers using an automated DNA synthesizer.(PE BioSystems Expedite 8909). Typically, 500 angstrom controlled-pore glass supports were used at the 0.2 micromole scale. In the case of 5'-attachment, after the desired probe sequence had been assembled (using A, G, C, and T monomers), four hexaethylene oxide phosphoramidite monomers (Glen Research) were added to the 5'-terminus. The coupling wait time was extended to 15 minutes by modifying the synthesizer program. Additional hexaethylene oxide monomer units were added in the same way. C-6 Amino phosphoramidite (Glen Research) was then added to the 5' terminus; the coupling wait time was again extended to 15 minutes. The acetic anhydride capping step and the final acidic detritylation were eliminated. In the case of 3'-attachment, oligonucleotide synthesis began with a controlled-pore glass support bearing orthoganally protected primary hydroxyl and amino functionalities (Glen Research). Chain elongation began on the hydroxyl group, and the amino group remained protected during oligomer assembly, only being unveiled during the final deprotection. The first four monomers to be added were hexaethylene oxide units, followed by the standard A, G, C, and T monomers. All capture oligo sequences were cleaved from the solid support and deprotected with ammonium hydroxide, concentrated to dryness, precipitated in ethanol, and purified by reverse-phase HPLC using an acetonitrile gradient in triethylammonium acetate buffer. Apppropriate fractions from the HPLC were collected, evaporated to dryness in a vacuum centrifuge, and then coevaporated with a portion of water.

Figure 3:
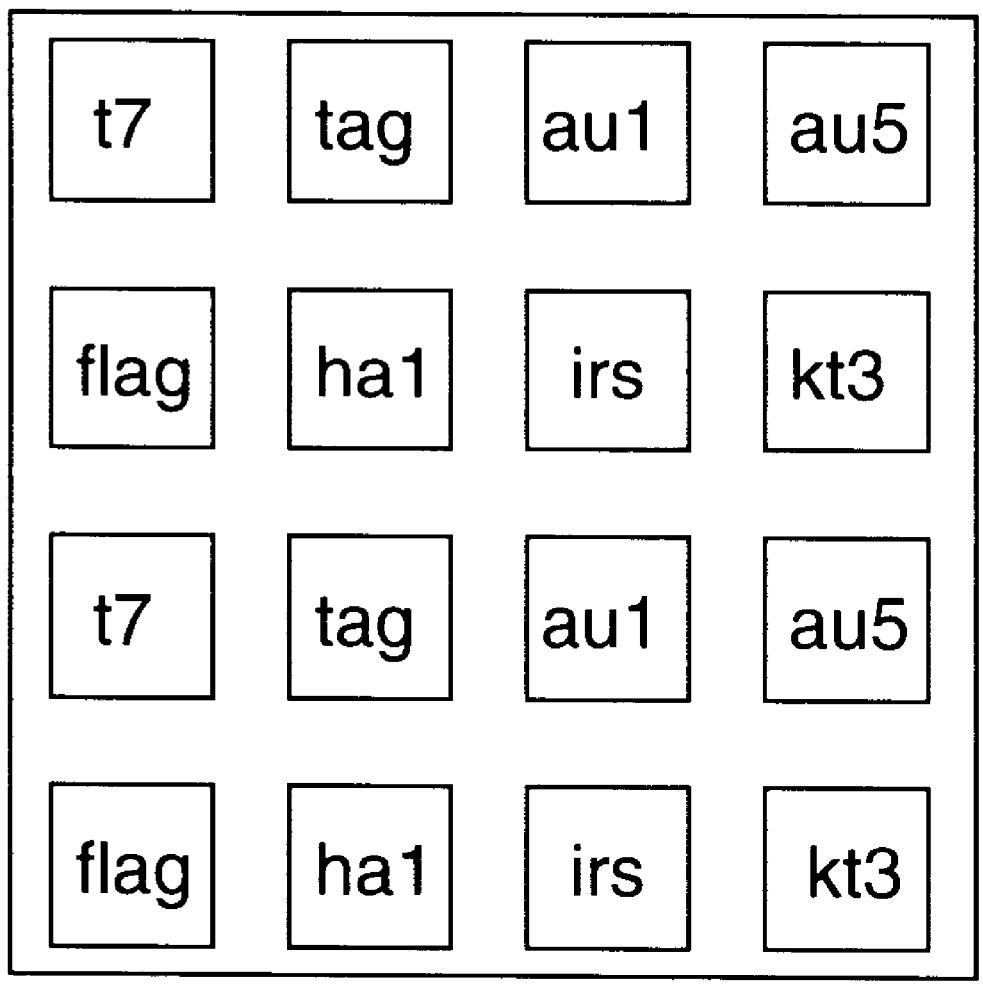
FIG. 3 is a schematic diagram of the layout of the FLAG and HA11 fusion chip capture probes utilized in FIGS. 4 and 5. In this Figure, t7, tag, au1, au5, flag, ha1, irs, and kt3 represent the capture probes CPt7 (positive control), CPtag (positive control), CPau1 (negative control), CPau5 (negative control), CPflag, CPha11, CPirs (negative control), and CPkt3 (negative control), respectively.

To attach the purified, amine-labeled capture oligos, the oligos were adjusted to a concentration of 250 micromolar in 50 mM sodium carbonate buffer (pH 9.0) containing 10% glycerol. The oligos were then robotically applied (MicroGrid, BioRobotics) to the derivatized glass surface described above at defined positions in a 5×5×16 array pattern (384 spots) within a 20×20 mm area. The layout of these capture probes is shown schematically in FIG. 3. A 16-pin tool was used to transfer the liquid, producing 200 micron features with a pitch of 600 microns. Each sub-grid of 24 spots represented a single capture probe (i.e., 24 duplicate spots). The array was incubated at room temperature in a moisture-saturated environment for 12–18 hours. The attachment reaction was terminated by immersing the glass surface in an aqueous 1% ammonia solution for five minutes with gentle agitation. The glass surface was then subjected to three 5-minute washes, using fresh portions of distilled water for each wash. The array was then soaked in a 10×PBS (phosphate buffered saline) solution for 2 hours at room temperature, and then rinsed again for 5 minutes in distilled water.

RNA-protein fusions between the peptides containing the FLAG and HA11 epitopes and their corresponding mRNAs were produced as generally described by Szostak et al., WO 98/31700; and Roberts and Szostak, Proc. Natl. Acad. Sci. USA 94:12297–12302, 1997. The polymerase chain reaction using Taq polymerase (Promega) was used to amplify the sequences 5'-TAA TAC GAC TCA CTA TAG GGA CAA TTA CTA TTT ACA ATT ACA ATG GAC TAC AAG GAC GAT GAC GAT AAG GGC GGC TGG TCC CAC CCC CAG TTC GAG AAG (SEQ ID NO: 12) and 5'-TAA TAC GAC TCA CTA TAG GGA CAA TTA CTA TTT ACA ATT ACA ATG TAC CCC TAC GAC GTG CCC GAC TAC GCC GGC GGC TGG TCC CAC CCC CAG TTC GAG AAG (SEQ ID NO: 13) for FLAG and HA11, respectively, using the oligonucleotide primers 5'-TAA TAC GAC TCA CTA TAG GGA CAA TTA CTA TTT ACA ATT (SEQ ID NO: 14) and 5'-AGCGGATGCCTTCTCGAACTGGGGGTGGGA (SEQ ID NO: 15). The resulting PCR products were transcribed in vitro using T7 RNA polymerase (Ambion) to produce an mRNA containing the coding region for the FLAG and HA11 epitopes and the TMV untranslated region. This RNA was ligated to a DNA linker 5'-AAA AAA AAA AAA AAA AAA AAA AAA AAA CC (SEQ ID NO: 3) containing a 5' phosphate and a 3' puromycin by T4 DNA ligase (Promega) in the presence of an 80:20 mixture of the following two DNA splints: 5'-TGCAACGACCAACTTTTTTTTTAGCGCATGC (SEQ ID NO: 16) and 5'-TGCAACGACCAACTTTTTTTTNAGCGCATGC (SEQ ID NO: 17), each containing two biotin moieties at the 5' terminus. The resulting RNA-DNA chimera was purified by binding to Immobilized NeutrAvidin (Pierce), washing to remove unligated material, and eluting by displacement using the sequence 5'-GCATCCGCTAAAAAAAAAAGTTGGTCGTTGC (SEQ ID NO: 18). Subsequent translations were performed in rabbit reticulocyte lysate (Ambion) according to the manufacturer's instructions except that MgCl$_2$ (150 mM) and KCl (425 mM) were added after 30 minutes to promote the formation of the puromycin-peptide bond. The RNA-peptide fusions were then purified by oligo dT affinity chromatography (Pharmacia), quantitated by scintillation counting of the incorporated vs. added $^{35}$S methionine (Amersham), and concentrated to a low volume via membrane filtration (MicroCon).

For hybridization of the fusions to the immobilized capture probes, aliquots of each of the FLAG and HA11 fusions, corresponding to 1.0 picomole each, were combined and adjusted to 5×SSC (saline sodium citrate)+0.02% Tween-20 in a volume of 20 microliters. The solution was applied to the glass chips described above, coverslips were placed on top, and the slides were placed in a moisture-saturated chamber at room temperature. After 18 hours the coverslips were removed, and the slides were washed sequentially with stirred 500 mL portions of 1×SSC+0.02% Tween-20, 1×SSC+0.02% Tween-20, and 1×SSC for 5 minutes each, followed by a brief rinse with 0.2×SSC. After removal of liquid the slides were allowed to briefly air-dry.

Figure 4:
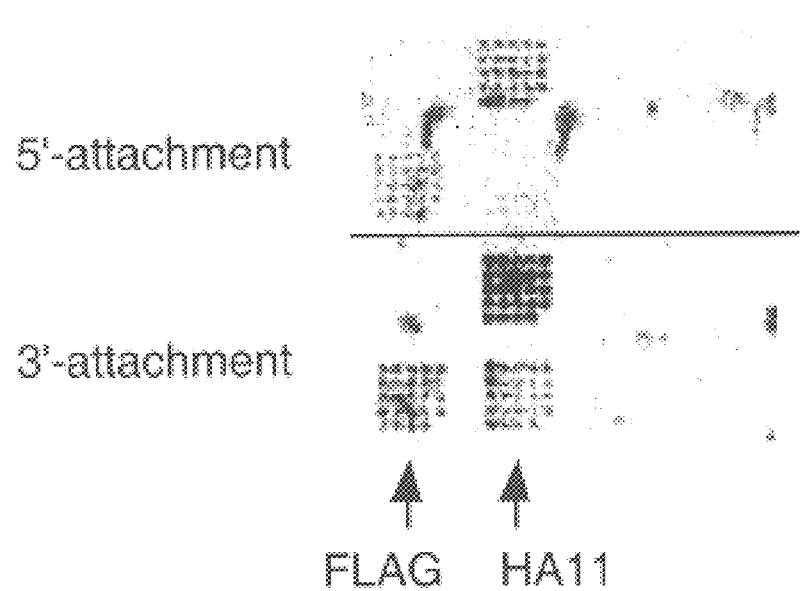
FIG. 4 is a phosphorimage demonstrating hybridization of nucleic acid-protein fusions (FLAG and HA11) to capture probes immobilized on a chip.

To detect hybridization, the FLAG and HA11-fusion chip was exposed to a phosphorimage screen (Molecular Dynamics) for 60 hours by direct contact between the screen and the chip. This allowed identification of the areas that contained hybridized fusions, since the peptides contained a $^{35}$S methionine radiolabel which was detectable by the phosphor storage screen. As shown in FIG. 4, analysis of the phosphorimage revealed that the fusions had successfully hybridized to their respective capture probes targeting specific areas of the RNA message (i.e., CPflag and CPha11). In addition, the four non-sense capture probes, which were not compelementary to any region of the FLAG or HA11 RNA, did not give any appreciable signal (i.e., CPau1, CPau5, CPirs, CPkt3). The positive control capture probe CPtag produced the expected signal, but the corresponding positive control capture probe CPt7 did not, likely due to degradation (e.g., exonuclease contamination) of the 5'-region of the targeted RNA. These results demonstrated the feasibility of addressing a mixture of peptides (as fusions) to specific locations on the surface of a chip. Both the 3'-attached capture probes and the 5'-attached capture probes were effective.

Figure 5:
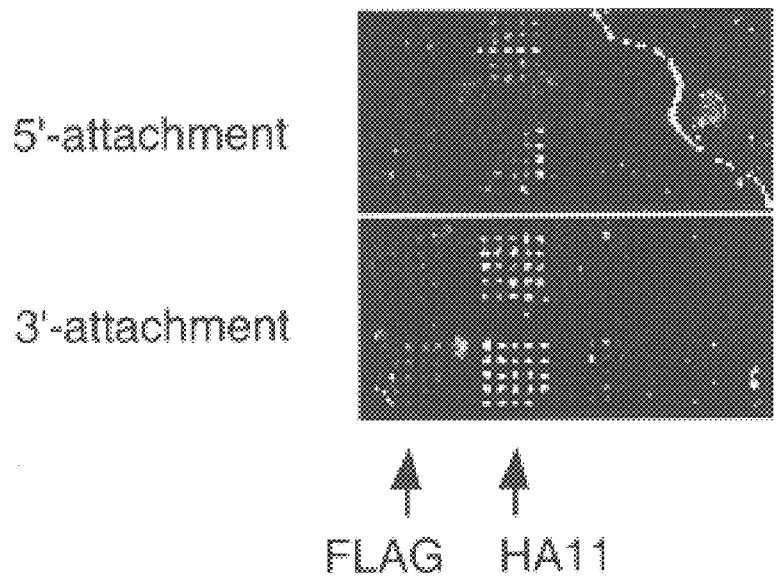
FIG. 5 is a fluorimage demonstrating hybridization of nucleic acid-protein fusions (FLAG and HA11) to capture probes immobilized on a chip and subsequent recognition with anti-HA11 monoclonal antibodies.

A duplicate chip was probed with a monoclonal antibody that recognized the HA11 epitope. All of the following steps were performed at 4° C. Nonspecific sites were first blocked with a solution containing 1×PBS (phosphate buffered saline)+1% BSA (bovine serum albumin, RNAse free grade, Ambion)+0.02% Tween-20 for 1 hour under a coverslip. The blocking solution was removed and 50 microliters of HA.11 monoclonal antibody (100:1 dilution, Berkeley Antibody Co.) in 1×PBS+0.02% Tween-20 was applied to the chip under a coverslip. After 2 hours the coverslip was removed, and the chip was washed with three 50 mL portions of 1×PBS+0.02% Tween-20 for 5 minutes each, with gentle agitation. Excess liquid was removed and then 50 microliters of Cy3-labeled goat anti-mouse IgG (400:1 dilution, Amersham Pharmacia Biotech) in 1×PBS+0.02% Tween-20 was added under a coverslip. After 1 hour the coverslip was removed, and the chip was washed in three 50mL portions of 1×PBS+0.02% Tween-20 for 5 minutes each, with gentle agitation. Excess liquid was removed, and the chip was allowed to air-dry at room temperature. The chip was subsequently analyzed at 10 micron pixel resolution with a confocal laser scanner (ScanArray 3000, General Scanning) using preset excitation and emission wavelengths tuned to the Cy3 fluorophore. As shown in FIG. 5, the resulting fluorimage was in accord with the phosphorimage and demonstrated that the HA11 peptide, which was covalently linked to its RNA message and fixed to the chip surface, was functional and was available to interact with its binding partner (the HA11 monoclonal antibody). Moreover, although both the FLAG-fusion and the HA11-fusion were presented on the chip surface, the HA11 monoclonal antibody was specific for its own epitope. In addition, the 3'-attachment capture probes generally provided a better signal than the 5'-attachment capture probes. Without being bound to a particular theory, this may reflect the greater accessibility of the epitope when it is oriented away from the chip surface.

EXAMPLE 8

Generation of an Exemplary Myc Fusion Chip

Using the techniques essentially as described above, an exemplary Myc fusion chip was also generated as follows.

For silylation of the glass surface, select grade, low-iron content, pre-cleaned 25×75 mm glass microscope slides (VWR Scientific, #48311-950) were used as supplied. A 1% solution of aminopropytrimethoxysilane (Gelest, Inc.) in 95% acetone/5% water was prepared and allowed to hydrolyze for 20 minutes. The glass slides were immersed in the hydrolyzed silane solution for 5 minutes with gentle agitation. Excess silane was removed by subjecting the slides to ten 5-minute washes, using fresh portions of 95% acetone/5% water for each wash, with gentle agitation. The slides were then cured by heating at 110° C. for 20 minutes.

To derivatize with a homobifunctional linker, the silane treated slides were immersed in a freshly prepared 0.2% solution of phenylene 1,4-diisothiocyanate (Aldrich Chemical Co.) in 90% DMF/10% pyridine for two hours, with gentle agitation. The slides were washed sequentially with 90% DMF/10% pyridine, methanol, and acetone. After air drying, the functionalized slides were stored at 0° C. in a vacuum desiccator over anhydrous calcium sulfate.

The capture oligos were synthesized based on the Myc sequence. In particular, the RNA employed to make the c-myc fusion (33 amino acids total) consisted of the following sequence: 5'-r(UAAUACGACUCACUAUAGGGA-CAAUUACUAUUUACAAUUACAAU GGGGACAA-UUACUAUUUACAAUUACAAUGGCUGAA-GAACAGAAACU GAUCUCUGAAGAAGAC-CUGCUGCGUAAACGUCGUGAACAGCUGAAAC ACAAACUGGAACAGCUGCGUAACUCUUGCGCU) (SEQ ID NO: 19). In addition, the following DNA linker, which also contains the essential puromycin moiety, was ligated to the 3'-terminus of the RNA message: 5'-d(AAAAAAAAAAAAAAAAAAAAAAAAAAAACC) (SEQ ID NO: 3). Three non-overlapping and thermodynamically isoenergetic 20-mer sequences along the RNA were identified to serve as capture points. In addition, dA25 (on the ligated DNA) was selected as a fourth target area. The targeted sequences began at nucleotide positions 1, 33, 80, and 125 (CP01, CP33, CP80 and CP125, respectively). A mismatch sequence, derived from target sequence 33 and containing four internal and adjacent nucleotide mismatches, was also designed (CPmm). A non-sense sequence, corresponding to the reverse-orientation of CP33, was also utilized as a negative control (CPns). The following is a list of the capture probe sequences that were employed (5' to 3') (SEQ ID NOS: 20–25):

CP 01: TTGTAAATAGTAATTGTCCC

CP33: AGAGATCAGTTTCTGTTCTT

CP80: AGTTTGTGTTTCAGCTGTTC

CP125: TTTTTTTTTTTTTTTTTTTTTTTTT

Cpmm: AGAGATCTCAATCTGTTCTT

Cpns: TTCTTGTCTTTGACTAGAGA

Oligonucleotide capture probes were chemically synthesized in the 3' to 5' direction by coupling standard phosphoramidite monomers with an automated DNA synthesizer (PE BioSystems Expedite 8909). Typically, 500 angstrom controlled-pore glass supports were used at the 0.2 micromole scale. After the desired probe sequence had been assembled (using A, G, C, and T monomers), hexaethylene oxide phosphoramidite monomer (Glen Research) was added to the 5'-terminus. The coupling wait time was extended to 15 minutes by modifying the synthesizer program. Additional hexaethylene oxide monomer units were added in the same way. C-6 Amino phosphoramidite (Glen Research) was then added to the 5' terminus; the coupling wait time was again extended to 15 minutes. The acetic anhydride capping step and the final acidic detritylation were eliminated. Capture oligo sequences were cleaved from the solid support and deprotected with ammonium hydroxide, concentrated to dryness, precipitated in ethanol, and purified by reverse-phase HPLC using an acetonitrile gradient in triethylammonium acetate buffer. Apppropriate fractions from the HPLC were collected, evaporated to dryness in a vacuum centrifuge, and then coevaporated with a portion of water.

Figure 6:
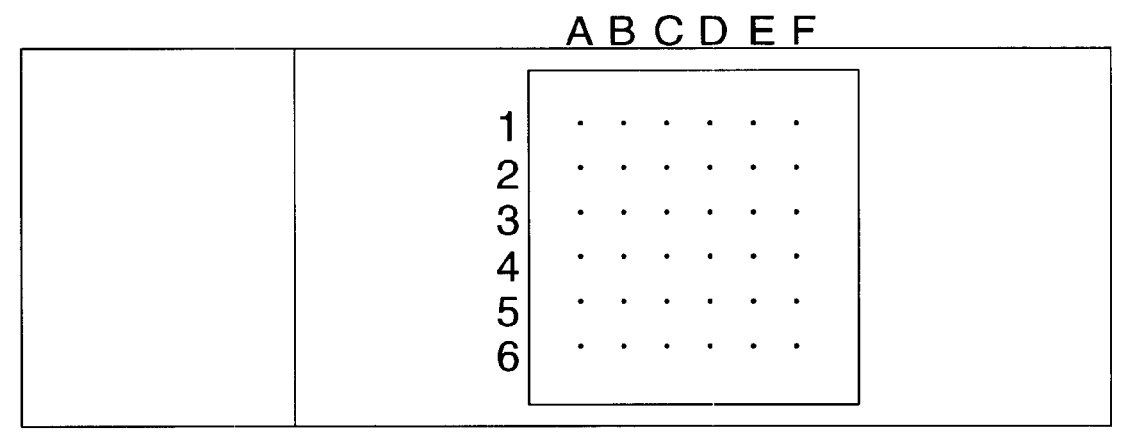

To attach these purified, amine-labeled capture oligos, the oligos were adjusted to a concentration of 500 micromolar in 100 mM sodium carbonate buffer (pH 9.0) and were applied to the derivatized glass surface at defined positions in a 6×6 array pattern (36 spots) within a 20×20 mm area (as shown in FIG. 6). CP01 was applied to locations A1, B1, C1 and A4, B4, C4. CP33 was applied to locations D1, E1, F1 and D4, E4, F4. CP80 was applied to locations A2, B2, C2 and A5, B5, C5. CP125 was applied to locations D2, E2, F2 and D5, E5, F5. Cpmm was applied to locations A3, B3, C3 and A6, B6, C6. Cpns was applied to locations D3, E3, F3 and D6, E6, F6. For manual deposition, aliquots of 0.2 microliter each were applied with a pipetman. The array was incubated at room temperature in a moisture-saturated environment for 12–18 hours. The attachment reaction was terminated by immersing the glass surface in an aqueous 1% ammonia solution for five minutes with gentle agitation. The glass surface was then subjected to three 5-minute washes, using fresh portions of distilled water for each wash. The array was then soaked in a 10×PBS (phosphate buffered saline) solution for 2 hours at room temperature, and then rinsed again for 5 minutes in distilled water.

RNA-protein fusions between a 33 amino acid peptide containing the c-myc epitope and its mRNA were produced as described by Szostak et al., WO 98/31700; and Roberts and Szostak, Proc. Natl. Acad. Sci. USA 94:12297–12302, 1997. The polymerase chain reaction using Taq polymerase (Promega) was used to amplify the sequence 5'-AGC GCA AGA GTT ACG CAG CTG TTC CAG TTT GTG TTT CAG CTG TTC ACG ACG TTT ACG CAG CAG GTC TTC TTC AGA GAT CAG TTT CTG TTC TTC AGC CAT (SEQ ID NO: 26) using oligonucleotide primers 5'-AGC GCA AGA GTT ACG CAG CTG (SEQ ID NO: 27) and 5'-TAA TAC GAC TCA CTA TAG GGA CAA TTA CTA TTT ACA ATT ACA ATG GCT GAA GAA CAG AAA CT (SEQ ID NO: 28). The resulting PCR product was transcribed in vitro using T7 RNA polymerase (Ambion) to produce an mRNA containing the coding region for the c-myc epitope and the TMV untranslated region. This RNA was ligated to a DNA linker 5'-AAA AAA AAA AAA AAA AAA AAA AAA AAA CC (SEQ ID NO: 3) containing a 5' phosphate and a 3' puromycin by T4 DNA ligase (Promega) in the presence of a DNA splint with the sequence TTT TTT TTT TAG CGC AAG A (SEQ ID NO: 29). The resulting 154mer RNA-DNA chimera was purified by denaturing polyacrylamide gel electrophoresis (6% acrylamide). Translation was performed in rabbit reticulocyte lysate (Ambion) according to the manufacturer's instructions except that KCl (500 mM) was added after 30 minutes to promote the formation of the puromycin-peptide bond. The RNA-peptide fusion was purified by oligo dT affinity chromatography (Pharmacia), quantitated by scintillation counting of the incorporated vs. added $^{35}$S methionine (Amersham), and dried to a pellet. 2.5 pmol of the c-myc fusion was produced.

To hybridize to the capture probes, the dry myc-fusion pellet was taken up with 20 microliters of 5×SSC (saline sodium citrate)+0.02% SDS, mixed, and then briefly centrifuged. The solution was applied to the slide described above, a coverslip was placed on top, and the slide was placed in a moisture-saturated chamber at room temperature. After 18 hours the coverslip was removed, and the slide was washed sequentially with stirred 500 mL portions of 5×SSC+0.02% SDS, 2.5×SSC+0.01% SSC, 2.5×SSC, and 1.25×SSC for 5 minutes each. After removal of liquid the slide was allowed to briefly air-dry.

Figure 7:
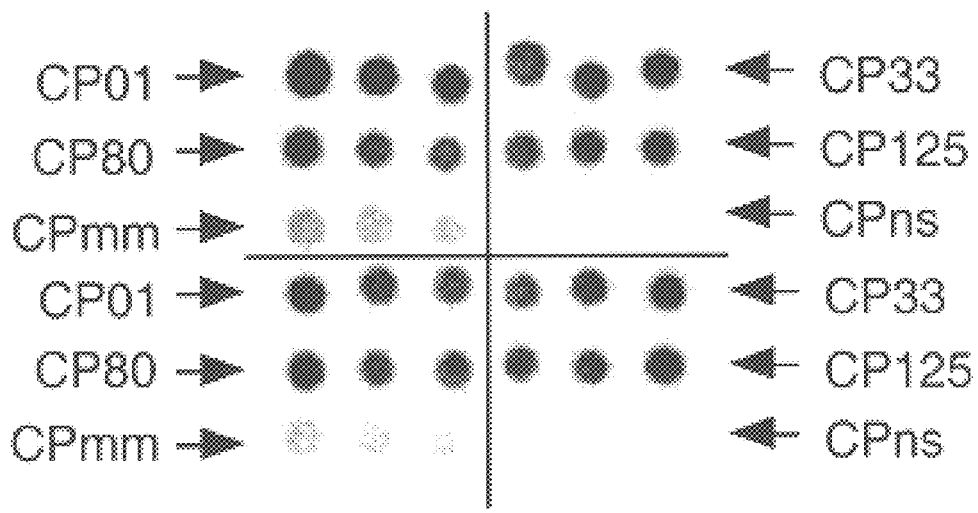
FIG. 7 is a phosphorimage demonstrating hybridization of nucleic acid-protein fusions (Myc) to capture probes immobilized on a chip.

To detect hybridization of the Myc fusions, the glass chip was exposed to a phosphorimage screen (Molecular Dynamics) for four hours by direct contact between the screen and the chip. This allowed identification of the areas that contained hybridized myc-fusion, since the myc peptide contained a $^{35}$S methionine radiolabel which was detectable by the phosphor storage screen. As shown in FIG. 7, analysis of the phosphorimage revealed that the myc-fusion had successfully hybridized to each of the four capture probes that targeted the myc RNA message and DNA linker sequence. In addition, the non-sense capture probe, which was not complementary to any region of the myc RNA, did not give any appreciable signal. The capture probe sequence that contained several mismatches produced only a small amount of signal. These results demonstrated that it was possible to address a peptide (as a fusion) to a specific location on the surface of a chip.

Figure 8:
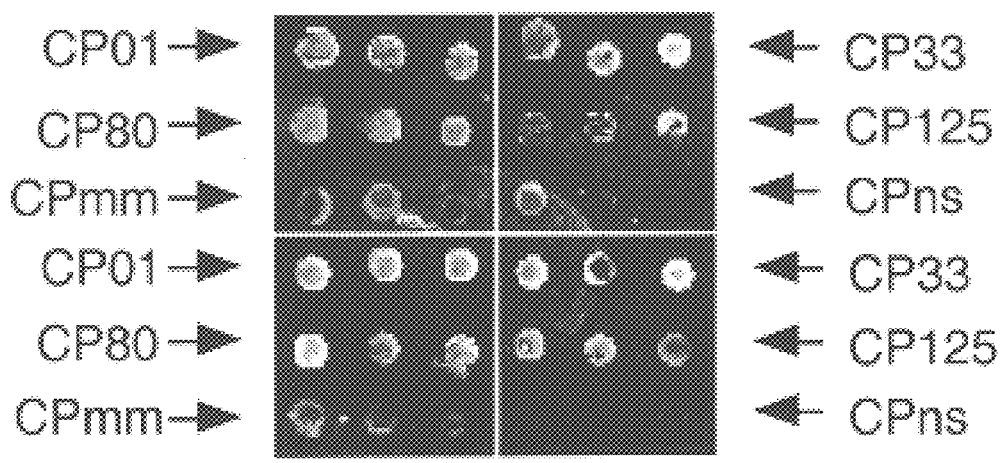
FIG. 8 is a fluorimage demonstrating hybridization of nucleic acid-protein fusions (Myc) to capture probes immobilized on a chip and subsequent recognition with anti-Myc monoclonal antibodies.

After phosphorimage analysis, the same chip was probed with a monoclonal antibody that recognized the c-myc epitope. All of the following steps were performed at 4° C. Nonspecific sites were first blocked with a solution containing 1×PBS (phosphate buffered saline)+1% BSA (bovine serum albumin, Sigma Chemical Co.)+0.1 unit per microliter RNAse inhibitor (Ambion) for 1 hour under a coverslip. The blocking solution was removed, and 50 microliters of 9E10 monoclonal antibody in 1×PBS (400:1 dilution, Berkeley Antibody Co.) was applied to the chip under a coverslip. After 1 hour the coverslip was removed, and the chip was washed with three 50 mL portions of 1×PBS for 5 minutes each, with gentle agitation. Excess liquid was removed, and then 50 microliters of Cy3-labeled goat anti-mouse IgG in 1×PBS (400:1 dilution, Amersham Pharmacia Biotech) was added under a coverslip. After 1 hour the coverslip was removed, and the chip was washed in three 50 mL portions of 1×PBS for 5 minutes each, with gentle agitation. Excess liquid was removed, and the chip was allowed to air-dry at room temperature. The chip was subsequently analyzed at 10 micron pixel resolution with a confocal laser scanner (ScanArray 3000, General Scanning) using preset excitation and emission wavelengths tuned to the Cy3 fluorophore. As shown in FIG. 8, the resulting fluorimage was in accord with the phosphorimage and demonstrated that the myc peptide, which was covalently linked to its RNA message and fixed to the chip surface, was functional and was available to interact with its binding partner (the monoclonal antibody).

All publications and patents mentioned in this specification are herein incorporated by reference to the same extent as if each individual publication or patent was specifically and individually indicated to be incorporated by reference.

OTHER EMBODIMENTS

From the foregoing description, it will be apparent that variations and modifications may be made to the invention described herein to adopt it to various usages and conditions. Such embodiments are also within the scope of the following claims.

---

What is claimed is:

1. A method for generating an addressable array of molecules, said method comprising:

(a) providing a solid support having a linker layer on its surface, said linker layer linking to derivatized capture probes, each of said capture probes comprising a non-nucleosidic spacer group located proximal to the linker layer and an oligonucleotide sequence located distal to the linker layer, said capture probes immobilized as an array on said solid support, wherein said oligonucleotide sequence is complementary to that of an addressable molecule; and (b) contacting said solid support with a population of addressable molecules whereby said addressable molecules orient themselves on said solid support by sequence-dependent recognition of and binding to said oligonucleotide sequences of said capture probes, wherein an addressable array of molecules is generated.

2. The method of claim 1, wherein said sequence-dependent recognition and binding comprises base pairing.

3. The method of claim 1, wherein said solid support is a glass or silica-based chip.

4. The method of claim 1, wherein said spacer group comprises a polyalkylene oxide.

5. The method of claim 1, wherein said spacer group comprises polyethylene oxide.

6. The method of claim 1, wherein said spacer group comprises hexaethylene oxide.

7. The method of claim 1, wherein each of said capture probes comprises a photocleavable linker.

8. The method of claim 1, wherein said oligonucleotide sequence comprises a modified base.

9. The method of claim 8, wherein said modified base is 5-propyne pyrimidine.

10. The method of claim 1, wherein said oligonucleotide sequence comprises an internucleotide analog.

11. The method of claim 10, wherein said internucleotide analog is a 3'-phosphoramidate linkage.

12. The method of claim 1, wherein said oligonucleotide sequence comprises a carbohydrate modification.

13. The method of claim 12, wherein said carbohydrate modification is a 2'-O-methyl group.

14. The method of claim 1, wherein each of said capture probes further comprises a reactive moiety.

15. The method of claim 14, wherein said reactive moiety is a primary amino group.

16. The method of claim 1, wherein, after said contacting step, said addressable molecule is covalently linked to said capture probe.

17. The method of claim 16, wherein said capture probe comprises one or more psoralen moieties.

18. The method of claim 1, wherein said array of addressable molecules comprises at least $10^2$ different molecules/cm$^2$.

19. The method of claim 18, wherein said array of addressable molecules comprises at least $10^4$ different molecules/cm$^2$.

20. The method of claim 1, wherein said array of addressable molecules is arrayed on a 125×80 mm surface.

21. The method of claim 1, wherein said array of addressable molecules is arrayed on a 10×10 mm surface.

22. The method of claim 1, wherein said array of addressable molecules is a two-dimensional array.

23. The method of claim 1, wherein each of said capture probes is covalently bound to said solid support.

24. The method of claim 1, wherein said addressable array of molecules is an array of nucleic acid-protein fusions.

25. The method of claim 24, wherein said nucleic acid-protein fusions are RNA-protein fusions.

26. The method of claim 24, wherein the protein is encoded by the nucleic acid.

27. The method of claim 24, wherein the nucleic acid-protein fusion comprises a hybridization tag sequence.

28. The method of claim 27, wherein said hybridization tag sequence comprises a modified base.

29. The method of claim 27, wherein said hybridization tag sequence comprises an internucleotide analog.

* * * * *